(12) United States Patent
Suh et al.

(10) Patent No.: US 11,141,369 B2
(45) Date of Patent: Oct. 12, 2021

(54) HUMAN ANTIBODY SPECIFICALLY BINDING TO ACNE BACTERIA USING PHAGE DISPLAY TECHNIQUE, AND USE THEREOF

(71) Applicant: E&S HEALTHCARE CO., LTD., Daejeon (KR)

(72) Inventors: Kyong Hoon Suh, Daejeon (KR); Suhn Kee Chae, Daejeon (KR); Eun Hye Kang, Daejeon (KR); Jong Hwan Jung, Daejeon (KR); Ki Se Lee, Sejong (KR); Sun Gi Koh, Daejeon (KR); Sang Ok Seo, Daejeon (KR); Dong Woo Lim, Sejong (KR); Seong Chan Choi, Daejeon (KR)

(73) Assignee: E&S Healthcare Co., Ltd., Daejeon (KR)

( * ) Notice: Subject to any disclaimer, the term of this patent is extended or adjusted under 35 U.S.C. 154(b) by 0 days.

(21) Appl. No.: 16/309,582

(22) PCT Filed: Jun. 13, 2017

(86) PCT No.: PCT/KR2017/006156
§ 371 (c)(1),
(2) Date: Dec. 13, 2018

(87) PCT Pub. No.: WO2017/217744
PCT Pub. Date: Dec. 21, 2017

(65) Prior Publication Data
US 2019/0224101 A1    Jul. 25, 2019

(30) Foreign Application Priority Data

Jun. 13, 2016 (KR) .................. 10-2016-0073186
Jun. 13, 2017 (KR) .................. 10-2017-0074010

(51) Int. Cl.
| | | |
|---|---|---|
| A61K 8/64 | (2006.01) | |
| A61Q 19/00 | (2006.01) | |
| A61Q 17/00 | (2006.01) | |
| A61P 31/04 | (2006.01) | |
| C07K 16/12 | (2006.01) | |
| A61P 17/10 | (2006.01) | |
| C07H 21/00 | (2006.01) | |
| A61K 39/00 | (2006.01) | |

(52) U.S. Cl.
CPC .............. *A61K 8/64* (2013.01); *A61P 17/10* (2018.01); *A61P 31/04* (2018.01); *A61Q 17/005* (2013.01); *A61Q 19/00* (2013.01); *C07H 21/00* (2013.01); *C07K 16/1267* (2013.01); *C07K 16/1292* (2013.01); *A61K 2039/507* (2013.01); *C07K 2317/21* (2013.01); *C07K 2317/622* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2011/0243960 A1 | 10/2011 | Gallo et al. |
| 2013/0123132 A1 | 5/2013 | Roge |
| 2014/0234337 A1 | 8/2014 | Tsukamoto |

FOREIGN PATENT DOCUMENTS

| | | |
|---|---|---|
| JP | 2013-147471 A | 8/2013 |
| KR | 10-1995-0002765 A | 2/1995 |
| KR | 10-2010-0003753 A | 1/2010 |

OTHER PUBLICATIONS

Skolnick et al. (Trends in Biotechnology 18: 34-39, 2000).*
Greenspan et al. (Nature Biotechnology 7: 936-937, 1999).*
Giusti et al. (Proc. Natl. Acad. Sci. USA. May 1987; 84 (9): 2926-2930).*
Winkler et al (J. Imm., 265:4505-4514, 2000).*
Caldas et al. (Mol. Immunol. May 2003; 39 (15): 941-952).*
Chien et al. (Proc. Natl. Acad. Sci. USA. Jul. 1986; 86 (14): 5532-5536).*
Casadevall et al. (PNAS, vol. 109 No. 31, pp. 12272-12273).*
Jung, Y.S. et al., "Generation of Human Monoclonal Antibodies against Propionibacterium Acnes by Applying the Phage Display Method to Human Peripheral Blood Mononuclear Cells Immunized in Vitro", Cytotechnology, vol. 57, pp. 169-175 (2008).
International Search Report cited in PCT/KR2017/006156 dated Oct. 19, 2017, 3 pages.
Teruaki Nakatsuji et al., "Antibodies Elicited by Inactivated Propionibacterium acnes-Based Vaccines Exert Protective Immunity and Attenuate the IL-8 Production in Human Sebocytes: Relevance to Therapy for Acne Vulgaris", J Invest Dermatol, Oct. 2008; 128(10): 2451-2457.
Jung et al., "Generation of human monoclonal antibodies against Propionibacterium acnes by applying the phage display method to human peripheral blood mononuclear cells immunized in vitro", Cytotechnology (2008) vol. 57, issue 2, pp. 169-175.
Jung et al., "Generation of Human Monoclonal Antibody Specific for Propionibacterium Acnes by In Vitro Immunization", Animal Cell Technology: Basic and Applied Aspects (2009) vol. 15, pp. 123-127.

* cited by examiner

*Primary Examiner* — Robert A Zeman
(74) *Attorney, Agent, or Firm* — Rothwell, Figg, Ernst & Mabeck, P.C.

(57) ABSTRACT

The present invention relates to a human antibody specifically binding to an acne-inducing bacterium using phage display technology and a use thereof, and more particularly, an antibody specifically binding to an antigen; a human antibody including the same; phage display technology using the same; and a cosmetic composition and a pharmaceutical composition using the same.

5 Claims, 10 Drawing Sheets
Specification includes a Sequence Listing.

HUMAN ANTIBODY SPECIFICALLY BINDING TO ACNE BACTERIA USING PHAGE DISPLAY TECHNIQUE, AND USE THEREOF

CROSS REFERENCE TO RELATED APPLICATION

This application is a 35 U.S.C. 371 National Phase Entry Application from PCT/KR2017/006156, filed Jun. 13, 2017, which claims the benefit of Korean Patent Application Nos. 10-2016-0073186, filed Jun. 13, 2016 and 10-2017-0074010 filed on Jun. 13, 2017, the disclosures of which are incorporated herein in their entirety by reference.

The instant application contains a Sequence Listing which has been submitted via EFS-Web and is hereby incorporated by reference in its entirety. Said Sequence Listing, created on Dec. 11, 2018, is named SOP114546US_Sequence Listing. ST25.Txt and is 13 kilobytes in size.

TECHNICAL FIELD

The present invention relates to a human antibody specifically binding to an acne-inducing bacterium using phage display technology and a use thereof, and more particularly, to an antibody specifically binding to *Propionibacterium acnes* (*P. acnes*), and a cosmetic composition and a pharmaceutical composition using the same.

BACKGROUND ART

While the cause of acne has not been clearly defined, acne is a localized chronic inflammatory skin disease resulting from inflammatory responses caused by multiple causes such as the increase in sebum secretion from the face, neck, chest, back or shoulder, abnormal keratinization in hair follicles, colony formation of acne-inducing bacteria, *P. acnes*.

Acne is a common skin disease which frequently occurs in 85% of teenagers and 11% of adults, and usually occurs in the early teens and decreases in adults, but may occur or may even be severe in adults. Adolescent acne more frequently occurs in males, but adult acne occurs more frequently in females, which results from changes in female hormones. In women, the secretion of progesterone, which is involved in premenstrual implantation, is increased and stimulates the secretion of a male hormone, thereby worsening the symptoms of adult acne. *P. acnes*, which is an acne-inducing bacterium, is an aerotolerant anaerobic bacterium, and is found in the skin of most healthy adults, and *P. acnes* is an opportunistic pathogen which does not cause diseases in normal persons, and is involved in various inflammatory diseases such as prosthetic joint infection, endocarditis, sarcoidosis, endophthalmitis and bacteremia as well as acne.

*P. acnes* obtains nutrients by degrading fatty acids and triglycerides of the sebum in the hair follicle into short chain fatty acids and propionic acid by secreting various types of enzymes under anaerobic conditions in the hair follicles. *P. acnes* forms colonies in the hair follicles, damages peripheral cells, and degrades sebum, thereby generating various types of by-products. The by-products block the hair follicles, and an inflammatory response is caused by the human immune system, resulting in acne.

Therefore, while various methods including local application (clindamycin, erythromycin, etc.) and oral administration (retinoids, etc.) of antibiotics and hormones, surgical incision and UV therapy have been tried to treat acne, there is no successful therapeutic method yet. When an antibiotic or hormone is used for a long time, serious side effects such as resistance, liver toxicity, peptic ulcers and deformities may occur, and when a local application is used, there are side effects such as skin irritation, redness and dermatitis, and there is a problem in that penetration into the affected part is not easy. In addition, surgical incision may result in damage and a scar which may remain due to the skin incision, and UV therapy has a limit in that skin damage is caused by UV and special equipment is required.

Therefore, the phage display technology, first developed in 1990 by the Medical Research Council in England, is the technology of preparing a human antibody library to be expressed on the surface of a bacteriophage in the form of an antibody fragment (Fab or ScFv) to select antibody clones with respect to a specific antigen. The possibility of selecting almost all types of human recombinant monoclonal antibodies specifically reacting with antibodies from a single pot antibody library system had been suggested, and through application of phage display antibody technology, various antibody fragments (Fab or ScFv type) capable of being applied to diagnosis in the body or treatment may be acquired.

DISCLOSURE

Technical Problem

The present invention is directed to providing a monoclonal antibody specifically binding to *P. acnes*.

The present invention is also directed to providing a use of the monoclonal antibody.

Technical Solution

One aspect of the present invention provides a monoclonal antibody specifically binding to *P. acnes*.

Another aspect of the present invention provides an expression vector including a polynucleotide encoding the monoclonal antibody.

Still another aspect of the present invention provides a transformant which is transformed with the expression vector.

In one exemplary embodiment of the present invention, the monoclonal antibody may be any one selected from the group consisting of (a) to (d) below:

(a) an antibody including a heavy chain variable region including heavy chain CDR1 set forth in SEQ ID NO: 1, heavy chain CDR2 set forth in SEQ ID NO: 2, and heavy chain CDR3 set forth in SEQ ID NO: 3, and a light chain variable region including light chain CDR1 set forth in SEQ ID NO: 4, light chain CDR2 set forth in SEQ ID NO: 5 and light chain CDR3 set forth in SEQ ID NO: 6;

(b) an antibody including a heavy chain variable region including heavy chain CDR1 set forth in SEQ ID NO: 7, heavy chain CDR2 set forth in SEQ ID NO: 8, and heavy chain CDR3 set forth in SEQ ID NO: 9, and a light chain variable region including light chain CDR1 set forth in SEQ ID NO: 10, light chain CDR2 set forth in SEQ ID NO: 11 and light chain CDR3 set forth in SEQ ID NO: 12;

(c) an antibody including a heavy chain variable region including heavy chain CDR1 set forth in SEQ ID NO: 13, heavy chain CDR2 set forth in SEQ ID NO: 14, and heavy chain CDR3 set forth in SEQ ID NO: 15, and a light chain variable region including light chain CDR1 set forth in SEQ ID NO: 16, light chain CDR2 set forth in SEQ ID NO: 17 and light chain CDR3 set forth in SEQ ID NO: 18; and (d) an antibody including a heavy chain variable region including heavy chain CDR1 set forth in SEQ ID NO: 19, heavy chain CDR2 set forth in SEQ ID NO: 20, and heavy chain CDR3 set forth in SEQ ID NO: 21, and a light chain variable region including light chain CDR1 set forth in SEQ ID NO: 22, light chain CDR2 set forth in SEQ ID NO: 23 and light chain CDR3 set forth in SEQ ID NO: 24.

In one exemplary embodiment of the present invention, the monoclonal antibody may be any one selected from the group consisting of (a) to (d) below:

(a) an antibody including a heavy chain variable region set forth in SEQ ID NO: 25 and a light chain variable region set forth in SEQ ID NO: 26;

(b) an antibody including a heavy chain variable region set forth in SEQ ID NO: 27 and a light chain variable region set forth in SEQ ID NO: 28;

(c) an antibody including a heavy chain variable region set forth in SEQ ID NO: 29 and a light chain variable region set forth in SEQ ID NO: 30; and (d) an antibody including a heavy chain variable region set forth in SEQ ID NO: 31 and a light chain variable region set forth in SEQ ID NO: 32.

In one exemplary embodiment of the present invention, the monoclonal antibody may be a human antibody.

Yet another aspect of the present invention provides a cosmetic composition for preventing or improving acne, which includes the monoclonal antibody as an active ingredient.

Yet another aspect of the present invention provides a pharmaceutical composition for preventing or improving acne, which includes the monoclonal antibody as an active ingredient.

Advantageous Effects

The monoclonal antibody according to the present invention can specifically recognize and bind to an acne bacterium. Therefore, it is anticipated that an antibody binding to a compound or enzyme exhibiting an antibacterial activity against an acne bacterium is used to relieve or eliminate an acne symptom without a side effect.

Therefore, a cosmetic composition and a pharmaceutical composition, which include the monoclonal antibody according to the present invention as a raw material, and improve acne without resistance and a side effect although being used for a long period of time, can be provided.

MODES OF THE INVENTION

Figure 1B:
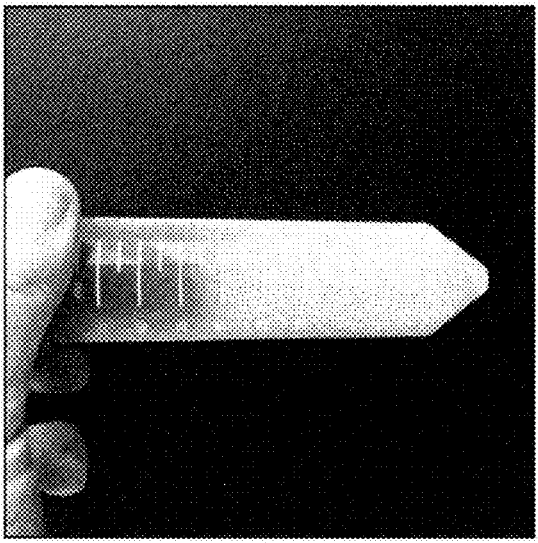
FIGS. 1A-1B are a set of images of *P. acnes* cultured in Reinforced clostridial medium (RCM) according to an exemplary embodiment of the present invention.

Hereinafter, terms and terminology used herein will be described.

The term "antibody" used herein includes immunoglobulin molecules which immunologically have reactivity with a specific antigen, and includes both polyclonal antibodies and monoclonal antibodies. In addition, the term "antibody" includes a form which is produced by a genetic engineering method, such as a chimeric antibody (e.g., a humanized murine antibody) and a heterologous antibody (e.g., a bispecific antibody). The term "antibody" also includes a single chain antibody, scAb, a derivative of the constant region of an antibody and an artificial antibody based on a protein scaffold, which have a function of binding to FcRn.

The term "monoclonal antibody" used herein is the term known in the art, and refers to a highly specific antibody directed against a single antigenic site. Generally, compared with a polyclonal antibody including different antibodies directed against different epitopes (antigenic determinants), the monoclonal antibody is directed against an antigenic single determinant. The monoclonal antibody has advantages of improving selectivity and specificity of diagnoses and analytic assays using antigen-antibody binding, and non-contamination with a different immunoglobulin since it is not synthesized by hybridoma culture.

Typically, an immunoglobulin includes a heavy chain and a light chain, each chain has a constant region and a variable region (the region is also known as a "domain"). The variable region of the light chain or the heavy chain includes three variable regions called complementarity determining regions (hereinafter, referred to as "CDRs"), and four framework regions. The CDR usually binds to an epitope of an antigen. The CDRs of each chain are sequentially named CDR1, CDR2 and CDR3, typically starting from the N-terminus, and are identified by a chain in which a specific CDR is located.

The term "variable" used herein means that antibodies have very different sequences in a specific region and binding specificity to a specific antigen. The variability of an antibody is not distributed uniformly throughout a variable domain of the antibody, but is centered on the CDRs. Each of the heavy and light chains of the monoclonal antibody has three CDRs, and at these regions, a surface antigen of an acne bacterium is recognized, thereby forming an antigen-antibody complex. Such CDR has a characteristic sequence for each monoclonal antibody, and to recognize a specific epitope, one monoclonal antibody may interact with some or all of six CDRs.

The term "phage display technology" used herein refers to technology of isolating scFv binding to an antibody by isolating only a phage which can significantly bind to a target antigen from a phage library. In this technology, the "panning" refers to a process of selecting only a phage displaying a peptide with a property of binding to a target molecule (an antibody, an enzyme, a cell surface receptor, etc.) on a surface from a phage library displaying a peptide on a phage coat. The above-described process is repeated three to 10 times to isolate a scFv having a significant binding ability to a target antigen, and finally, a humanized monoclonal antibody may be produced with the selected scFv.

Hereinafter, the present invention will be described in detail.

The present invention provides a monoclonal antibody specifically binding to P. acnes.

Specifically, the monoclonal antibody may include any one sequence selected from the group consisting of (a) to (d) below:

(a) an antibody including a heavy chain variable region including heavy chain CDR1 set forth in SEQ ID NO: 1, heavy chain CDR2 set forth in SEQ ID NO: 2, and heavy chain CDR3 set forth in SEQ ID NO: 3, and a light chain variable region including light chain CDR1 set forth in SEQ ID NO: 4, light chain CDR2 set forth in SEQ ID NO: 5 and light chain CDR3 set forth in SEQ ID NO: 6;

(b) an antibody including a heavy chain variable region including heavy chain CDR1 set forth in SEQ ID NO: 7, heavy chain CDR2 set forth in SEQ ID NO: 8, and heavy chain CDR3 set forth in SEQ ID NO: 9, and a light chain variable region including light chain CDR1 set forth in SEQ ID NO: 10, light chain CDR2 set forth in SEQ ID NO: 11 and light chain CDR3 set forth in SEQ ID NO: 12;

(c) an antibody including a heavy chain variable region including heavy chain CDR1 set forth in SEQ ID NO: 13, heavy chain CDR2 set forth in SEQ ID NO: 14, and heavy chain CDR3 set forth in SEQ ID NO: 15, and a light chain variable region including light chain CDR1 set forth in SEQ ID NO: 16, light chain CDR2 set forth in SEQ ID NO: 17 and light chain CDR3 set forth in SEQ ID NO: 18; and (d) an antibody including a heavy chain variable region including heavy chain CDR1 set forth in SEQ ID NO: 19, heavy chain CDR2 set forth in SEQ ID NO: 20, and heavy chain CDR3 set forth in SEQ ID NO: 21, and a light chain variable region including light chain CDR1 set forth in SEQ ID NO: 22, light chain CDR2 set forth in SEQ ID NO: 23 and light chain CDR3 set forth in SEQ ID NO: 24.

More specifically, the monoclonal antibody may be any one antibody selected from the group consisting of (a) to (d) below.

(a) an antibody including a heavy chain variable region set forth in SEQ ID NO: 25 and a light chain variable region set forth in SEQ ID NO: 26;

(b) an antibody including a heavy chain variable region set forth in SEQ ID NO: 27 and a light chain variable region set forth in SEQ ID NO: 28;

(c) an antibody including a heavy chain variable region set forth in SEQ ID NO: 29 and a light chain variable region set forth in SEQ ID NO: 30;

(d) an antibody including a heavy chain variable region set forth in SEQ ID NO: 31 and a light chain variable region set forth in SEQ ID NO: 32.

More specifically, a heavy chain variable region of the monoclonal antibody may include one or more amino acid sequences selected from the group consisting of SEQ ID NOs: 25, 27, 29 and 31 or a sequence having 80% or more, preferably 90% or more, and most preferably 95% or more identity with the above-mentioned sequence in the CDR region; and/or a light chain variable region may include one or more amino acid sequences selected from the group consisting of SEQ ID NOs: 26, 28, 30 and 32 or a sequence having 80% or more, preferably 90% or more, and most preferably 95% or more identity with the above-mentioned sequence in the CDR region.

The monoclonal antibody of the present invention may be used to detect P. acnes by detecting the formation of an antigen-antibody complex after reacting with a biological sample.

The term "antigen-antibody complex" used herein refers to a product of binding a P. acnes protein antigen in a sample and the monoclonal antibody according to the present invention recognizing the antigen, and the formation of the antigen-antibody complex may be detected by any method selected from the group consisting of a colorimetric method, an electrochemical method, a fluorimetric method, luminometry, a particle counting method, visual assessment and a scintillation counting method. However, the present invention is not limited thereto, and various applications are possible.

In the present invention, to detect the antigen-antibody complex, various markers may be used. Specifically, the marker may be selected from the group consisting of an enzyme, a fluorescent material, a ligand, a luminescent material, a microparticle and a radioactive isotope, but the present invention is not necessarily limited thereto. Preferably, the antigen-antibody complex is detected by enzyme-linked immunosorbent assay (ELISA). Various types of ELISA, for example, direct ELISA using a labeled antibody recognizing an antigen attached to a solid support, indirect ELISA using a labeled secondary antibody recognizing an antigen attached to a solid support, direct sandwich ELISA using a different labeled antibody recognizing an antigen in a complex of an antibody attached to a solid support and the antigen, and indirect sandwich ELISA using a labeled secondary antibody recognizing an antibody reacted with another antibody recognizing an antigen in a complex of an antibody attached to a solid support and the antigen, are used. The monoclonal antibody may have a detection marker, and when there is no detection marker, the monoclonal antibody may be captured, and detected by being treated with another antibody having a detection marker.

In addition, the present invention provides an expression vector, which includes a polynucleotide encoding the monoclonal antibody according to the present invention.

In addition, the present invention provides a transformant which is transformed with the expression vector.

It can be well understood by those of ordinary skill in the art that, in a polynucleotide encoding the antibody of the present invention, by codon degeneracy or in consideration of a preferred codon in an organism for expressing the antibody, a variety of changes may be made to a coding region within a range of not changing the amino acid sequence of an antibody expressed from the coding region, and a variety of changes or modifications may be made without affecting gene expression even in a part excluding the coding region, and such a modified gene is also included in the scope of the present invention. That is, as long as the polynucleotide of the present invention encodes a protein having equivalent activity therewith, one or more nucleic acid bases may be mutated by substitution, deletion, insertion or a combination thereof, and such mutants are also included in the scope of the present invention. The sequence of the polynucleotide may be single or double-stranded, and may be a DNA or RNA (mRNA) molecule.

To construct the expression vector, depending on the type of host cells for producing the antibody, an expression regulatory sequence such as a promoter, a terminator or an enhancer, or a sequence for membrane targeting or secretion may be suitably selected, and may be combined in various ways according to purpose.

The expression vector of the present invention may include a plasmid vector, a cosmid vector, a bacteriophage vector and a viral vector, but the present invention is not limited thereto. A suitable expression vector may include a signal sequence or leader sequence for membrane targeting or secretion, as well as expression regulatory elements such as a promoter, an operator, an initiation codon, a termination codon, a polyadenylation signal and an enhancer, and may be constructed in various ways according to purpose. The promoter of the expression vector may be constitutive or inducible. When a host is *Escherichia* sp. bacteria, a PhoA signal sequence or an OmpA signal sequence may be used, when a host is *Bacillus* sp. bacteria, an α-amylase signal sequence or a subtilisin signal sequence may be used, when a host is yeast, an MFa signal sequence or a SUC2 signal sequence may be used, when a host is animal cells, an insulin signal sequence, an α-interferon signal sequence or an antibody molecule signal sequence may be used, but the present invention is not limited thereto. In addition, the expression vector may include a selection marker for selecting host cells containing a vector, and a replicable expression vector includes a replication origin.

In addition, the present invention provides a method of producing a monoclonal antibody, which includes: 1) inoculating and culturing the transformant in a medium; and 2) purifying a monoclonal antibody specifically binding to *P. acnes* from the culture solution obtained in Step 1).

The expression vector according to the present invention may be introduced into suitable host cells, for example, *E. coli* or yeast cells, and the transformed host cells may be cultured to mass produce the antibodies according to the present invention. Suitable culture methods and medium conditions according to the type of host cells may be easily selected by those of ordinary skill in the art using technology known to those of ordinary skill in the art. The host cells may be prokaryotes such as *E. coli* or *Bacillus subtilis*. In addition, the host cells may be eukaryotic cells derived from yeast cells such as *Saccharomyces cerevisiae*, insect cells, plant cells or animal cells. More preferably, the animal cells may be a human-derived cell line. A method of introducing the expression vector into the host cells is any method known to those of ordinary skill in the art.

In addition, the present invention provides a cosmetic composition for preventing or improving acne, which includes the monoclonal antibody, which specifically binds to *P. acnes* according to the present invention, as an active ingredient.

In addition, the present invention provides a use of the monoclonal antibody to be used in the cosmetic composition for preventing or improving acne.

The cosmetic composition of the present invention includes components conventionally used in the cosmetic composition as well as the human antibody, and includes, for example, conventional additives such as an antioxidant, a stabilizer, a solubilizer, a vitamin, a pigment and a fragrance, and carriers.

In the monoclonal antibody of the present invention, the monoclonal antibody of the present invention may be generally contained at 0.1 to 50 wt %, and preferably 1 to 10 wt %.

The cosmetic composition of the present invention may be formulated in any form generally prepared in the art, for example, a solution, a suspension, an emulsion, a paste, a gel, a cream, a lotion, a powder, a soap, a surfactant-containing cleanser, oil, a powder-type foundation, an emulsion-type foundation, a wax-type foundation or a spray, but the present invention is not limited thereto. More specifically, the cosmetic composition may be formulated as a softening toner (skin), a nourishing toner (milk lotion), a nourishing cream, a massage cream, an essence, an eye cream, a cleansing cream, a cleansing foam, a cleansing water, a pack, a spray or a powder.

When the cosmetic composition of the present invention is formulated as a paste, a cream or a gel, animal oil, vegetable oil, wax, paraffin, starch, tragacanth, a cellulose derivative, polyethylene glycol, silicone, bentonite, silica, talc or zinc oxide may be used as a carrier component, and when the cosmetic composition of the present invention is formulated as a powder or spray, lactose, talc, silica, aluminum hydroxide, calcium silicate or polyamide powder may be used as a carrier component, and particularly, when the cosmetic composition of the present invention is formulated as a spray, a propellant such as a chlorofluorohydrocarbon, propane/butane or dimethyl ether may be additionally included.

When the cosmetic composition of the present invention is formulated as a solution or emulsion, a solvent, a solubilizer or an emulsifier may be used as a carrier component, and the carrier is, for example, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or an aliphatic ester of sorbitan.

When the cosmetic composition of the present invention is formulated as an emulsion, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar or tragacanth may be used as a carrier component.

When the cosmetic composition of the present invention is formulated as a surfactant-containing cleanser, an aliphatic alcohol sulfate, an aliphatic alcohol ether sulfate, sulfosuccinate monoester, isethionate, an imidazolinium derivative, methyl taurate, sarcosinate, a fatty acid amide ether sulfate, an alkylamido betaine, an aliphatic alcohol, aliphatic glyceride, aliphatic diethanolamide, vegetable oil, a lanolin derivative or ethoxylated glycerol fatty acid ester may be used as a carrier component.

In addition, the present invention provides a pharmaceutical composition for preventing or improving acne, which includes the monoclonal antibody specifically binding to *P. acnes* according to the present invention as an active ingredient.

In addition, the present invention provides a use of a pharmaceutical composition for preventing or improving acne, which includes the monoclonal antibody.

The monoclonal antibody of the present invention can be non-orally administered in clinical administration, and may be used in the form of a general medication. The non-oral administration may be, but is not limited to, intravenous, intramuscular, intraarterial, intramedullary, intrathecal, intracardial, transdermal, subcutaneous, intraperitoneal, intranasal, intestinal, local, sublingual or rectal administration.

For non-oral administration, the pharmaceutical composition according to the present invention may be formulated as an injection, a transdermal drug or a nasal aspirator with suitable non-oral carriers by a method known in the art. The injection has to be necessarily sterilized, and protected from contamination with microorganisms such as bacteria and fungi. A suitable carrier for the injection may be, but is not limited to, a solvent or dispersive medium such as water, ethanol, a polyol (e.g., glycerol, propylene glycol, liquid polyethylene glycol, etc.), a mixture thereof and/or vegetable oil. More preferably, an isotonic solution such as a Hank's solution, a Ringer's solution, phosphate buffered saline (PBS) or injectable sterile water containing triethanol amine, 10% ethanol, 40% propylene glycol and 5% dextrose may be used as a suitable carrier. To protect the injection from microbial contamination, various antibacterial agents and antifungal agents such as paraben, chlorobutanol, phenol, sorbic acid, thimerosal, etc. may be further included. In addition, the injection may further include an isotonic agent such as sugar or sodium chloride in most cases.

A transdermal drug may be an ointment, a cream, a lotion, a gel, a drug for external use, a paste, a liniment, or an aerosol. Here, the "transdermal administration" refers to the delivery of an effective amount of active ingredient contained in a pharmaceutical composition by locally administering the pharmaceutical composition into the skin.

In the case of an inhaler, the compound used according to the present invention may be conveniently delivered in the form of an aerosol spray from a pressurized pack or nebulizer using a suitable propellant such as dichlorofluoromethane, trichlorofluoromethane, dichlorotetrafluoroethane, carbon dioxide or a different appropriate gas. In the case of the pressurized aerosol, a dosage unit may be determined by providing a valve for delivering a measured amount. For example, a gelatin capsule and a cartridge, which are used in an inhaler or insufflator, may be formulated to contain a powder mixture of a compound and a suitable powder base such as lactose or starch. Formulations for non-oral administration are described in the protocols generally known in all of the pharmaceutical chemistry field (Remington's Pharmaceutical Science, 15th Edition, 1975. Mack Publishing Company, Easton, Pa. 18042, Chapter 87: Blaug, Seymour).

When containing the monoclonal antibody according to the present invention, the pharmaceutical composition according to the present invention preferably provides an effect of preventing or treating acne. The "effective amount" used herein refers to an amount at which a reaction occurs higher than that of a negative control, and preferably, an amount sufficient for exhibiting an effect of killing *P. acnes* bacteria or reducing acne. In the pharmaceutical composition according to the present invention, the monoclonal antibody according to the present invention may be contained at 0.01 to 99.99%, and a pharmaceutically acceptable carrier may be contained at the remaining content. The effective amount of the monoclonal antibody according to the present invention contained in the pharmaceutical composition according to the present invention may vary depending on the form in which the composition is produced.

A total effective amount of the pharmaceutical composition according to the present invention may be administered to a patient as a single dose, or may be administered according to a fractionated treatment protocol for long-term administration at multiple doses. The pharmaceutical composition according to the present invention may vary a content of the active ingredient according to the severity of a disease. In non-oral administration, based on the monoclonal antibody according to the present invention, the pharmaceutical composition may be administered daily such that the active ingredient is preferably administered at 0.01 to 50 mg, and more preferably, 0.1 to 30 mg per kg of body weight, and in oral administration, based on the monoclonal antibody according to the present invention, the pharmaceutical composition may be administered one to several times a day such that the active ingredient is preferably administered at 0.01 to 100 mg, and more preferably 0.01 to 10 mg per kg of body weight. However, an effective dose of the monoclonal antibody according to the present invention with respect to a patient is determined by considering various factors such as the patient's age, body weight, health condition, sex, the severity of a disease, a diet and an excretion rate, as well as an administration route and the frequency of administration of the pharmaceutical composition, and in terms of these factors, a suitably effective dose according to a specific use of the monoclonal antibody according to the present invention for preventing or treating acne may be determined by those of ordinary skill in the art. The pharmaceutical composition according to the present invention is not particularly limited in dosage form, administration route, and administration method as long as the effect of the present invention is exhibited.

The pharmaceutical composition according to the present invention may be used independently or in combination with surgery, radiation therapy, hormone therapy, chemotherapy or a method using a biological response modifier.

The pharmaceutical composition according to the present invention may also be prepared in the form of a preparation for external use, which includes the monoclonal antibody according to the present invention as an active ingredient.

When the pharmaceutical composition of the present invention is used as a skin preparation for external use, it may additionally contain an additive conventionally used in the dermatological field, like an optionally different ingredient conventionally used for a skin preparation for external use, such as a lipid material, an organic solvent, a solubilizer, a concentrate, a gelling agent, a softener, an antioxidant, an emulsifier, a stabilizer, a foaming agent, a flavoring agent, a surfactant, water, an ionic emulsifier, a non-ionic emulsifier, a filler, a metal ion inhibitor, a chelating agent, a preservative, a vitamin, a blocking agent, a wetting agent, essential oil, a dye, a pigment, a hydrophilic active agent, a hydrophilic active agent, a lipophilic active agent, or a lipid vesicle. In addition, the ingredients may be introduced at an amount generally used in the dermatological field. When the pharmaceutical composition of the present invention is provided as a skin preparation for external use, it may be prepared in the form of an ointment, a patch, a gel, a cream or a spray.

EXAMPLES

Hereinafter, the present invention will be described in further detail with reference to examples. The examples are merely provided to more fully describe the present invention, and it will be obvious to those of ordinary skill in the art that the scope of the present invention is not limited to the following examples.

Example 1

Culture of *P. acnes*

As antigenic bacteria for producing the monoclonal antibody of the present invention, acne-inducing *P. acnes* was cultured. Since *P. acnes*, a gram-positive bacterium, has a great number of antigens specific to the cell membrane, a human antibody which specifically recognizes and binds to the pathogen itself was produced.

Figure 1A:
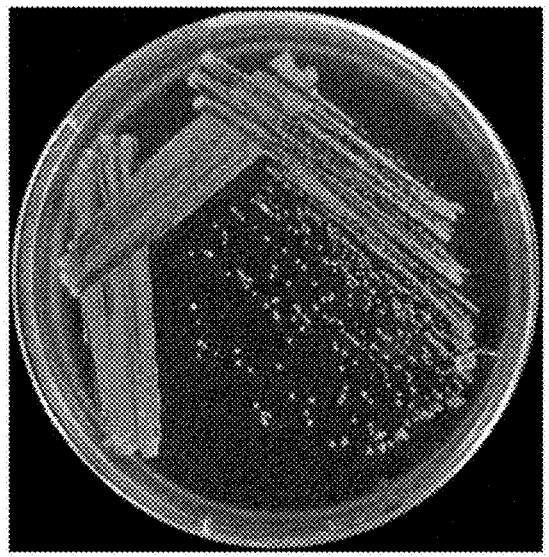

For sub-culturing in a solid medium, *P. acnes* was streaked on Reinforced clostridial medium (RCM), put into an anaerobic incubator or AnaeroPack™-Anaero (A-04, MGC), which was placed in a sealed box, and cultured at 37° C. for 5 days (FIG. 1A).

For culture in a liquid medium, 1.5 mL of Reinforced clostridial broth (RCM liquid medium) was put into a tube, inoculated with a colony of sub-cultured *P. acnes*, and the bacteria were subjected to static culture at 37° C. for 5 days. The cultured solution was centrifuged to obtain a cell pellet, and the cell pellet was suspended in a centrifuge tube filled with 50 mL of RCM broth and subjected to static culture again at 37° C. for 5 days (FIG. 1B).

Example 2

Production of Monoclonal Antibody Specifically Binding to *P. acnes*

Figure 2:
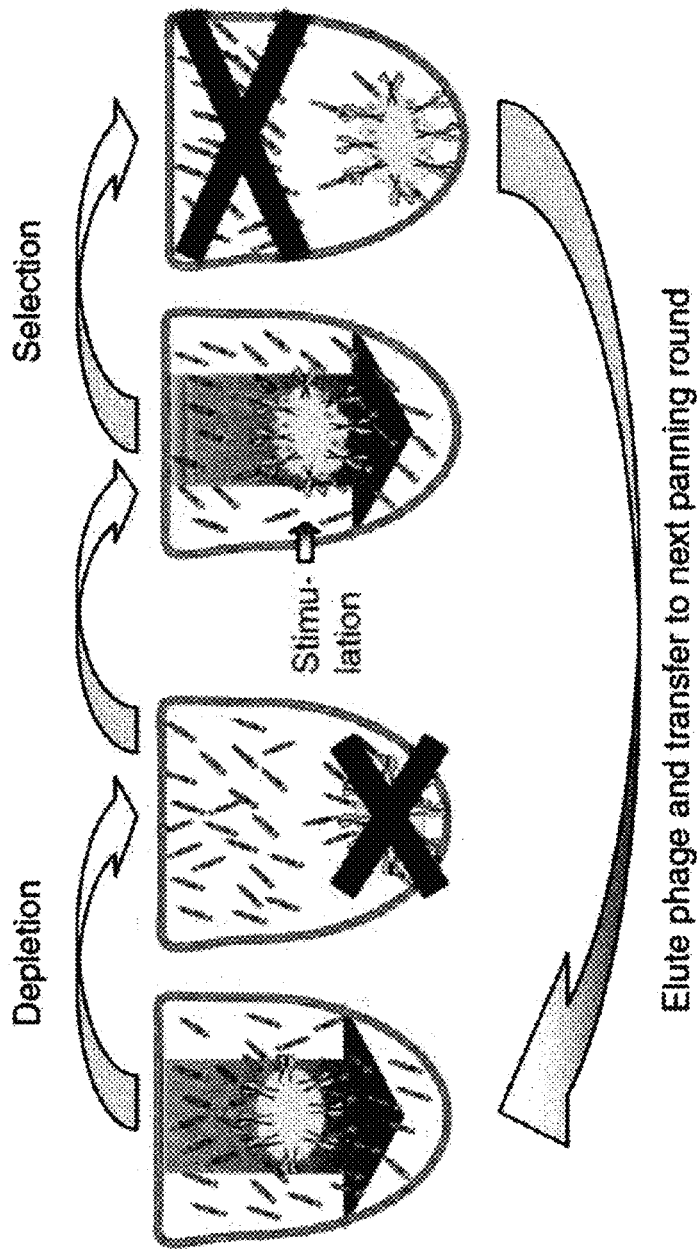
FIG. 2 is a diagram illustrating phage display technology according to an exemplary embodiment of the present invention.

<2-1> Construction of *P. acnes*-Binding Antibody Candidate Group Using Phage Display Technology To prepare a monoclonal antibody specifically binding to *P. acnes*, first, a *P. acnes*-binding antibody candidate group was prepared by phage display technology illustrated in the schematic diagram of FIG. 2.

Specifically, 1 mL of a human-derived scFv library phage having a diversity of $2.7 \times 10^{10}$ was reacted with 2 mL of *Staphylococcus epidermidis* for 2 hours, and scFv-phage which has a possibility of also binding to harmless bacteria in the skin was previously removed (Step 1). After removal, the remaining scFv-phage was reacted with *P. acnes* for 2 hours to elute the scFv-phage specifically binding to *P. acnes*, thereby obtaining poly-scFv-phage (Step 2). The obtained poly-scFv-phage was transfected into XL1-Blue for amplification, and the amplified poly-scFv-phage was subjected to processes of Step 1 and Step 2 in triplicate, thereby selectively amplifying phages with high affinity (panning step). The finally obtained poly-scFv-phage was diluted and subjected to titration, thereby determining an amplification level.

Figure 3A:
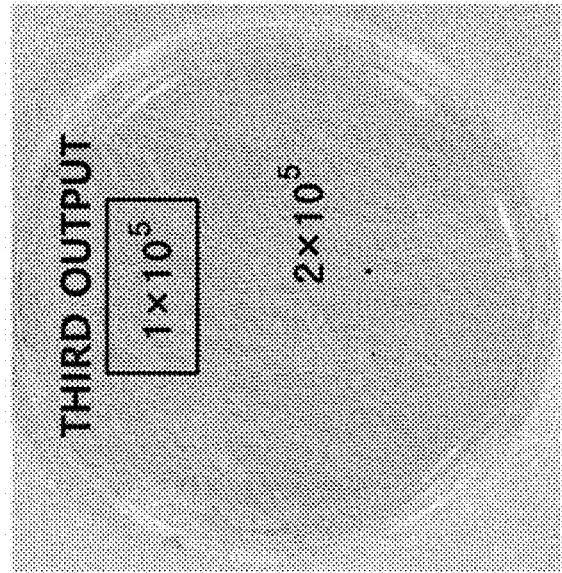
FIGS. 3A-3B are a set of images illustrating the third panning titration of *P. acnes* according to an exemplary embodiment of the present invention.
Figure 3B:
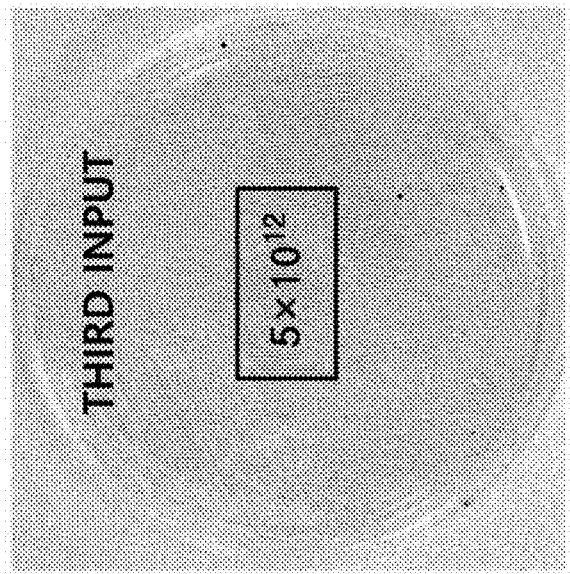

The levels of the phage candidate groups amplified in the panning step, respectively, are shown in Table 1 below. In the phage candidate groups, the number of scFv-phages included in 1 mL of a reaction solution before reaction with *P. acnes* was $1 \times 10^{13}$, $1.6 \times 10^{13}$ or $5 \times 10^{12}$, and the number of scFv-phages obtained by binding to *P. acnes* through the reaction was $2 \times 10^4$, $8 \times 10^4$ and $1 \times 10^5$, respectively (FIGS. 3A-3B).

TABLE 1

| Acne-inducing bacteria | First | Second | Third |
| --- | --- | --- | --- |
| Input | $1 \times 10^{13}$/ml | $1.6 \times 10^{13}$/ml | $5 \times 10^{12}$/ml |
| Output | $2 \times 10^4$/ml | $8 \times 10^4$/ml | $1 \times 10^5$/ml |

To confirm whether the selected poly-scFv-phage has affinity for *P. acnes*, the poly-scFv-phage in each group, obtained in the panning step, was subjected to ELISA.

For ELISA, first, *P. acnes* or control cells (*S. epidermidis*) were cultured, washed with PBS and diluted to have an absorbance of 0.5. The diluted cells were seeded at 100 μL per well of a 96-well plate, and cultured at 4° C. for 16 hours for coating. Afterward, the reaction solution in all wells was removed, 100 μL of PBSA was added to each well, cultured at 4° C. for 2 hours for blocking, and then the PBSA was removed. After the removal, 100 μL of the poly-scFv-phage-containing solution was added to each well, and incubated at 4° C. for 1 hour. Afterward, a process of washing including removing the reaction solution from all wells and adding 200 μL of diluted PBST to each well was performed in duplicate. After the washing, 100 μL of hFc-HRP diluted at 1:4000 was added to each well, and incubated at room temperature in a dark room for 10 minutes to induce a color reaction. To terminate the color reaction turning blue, 100 μL of a stop solution was added to each well, and when the color of the reactant turned yellow, an absorbance for each well was measured at 450 nm using a microplate reader.

Figure 4:
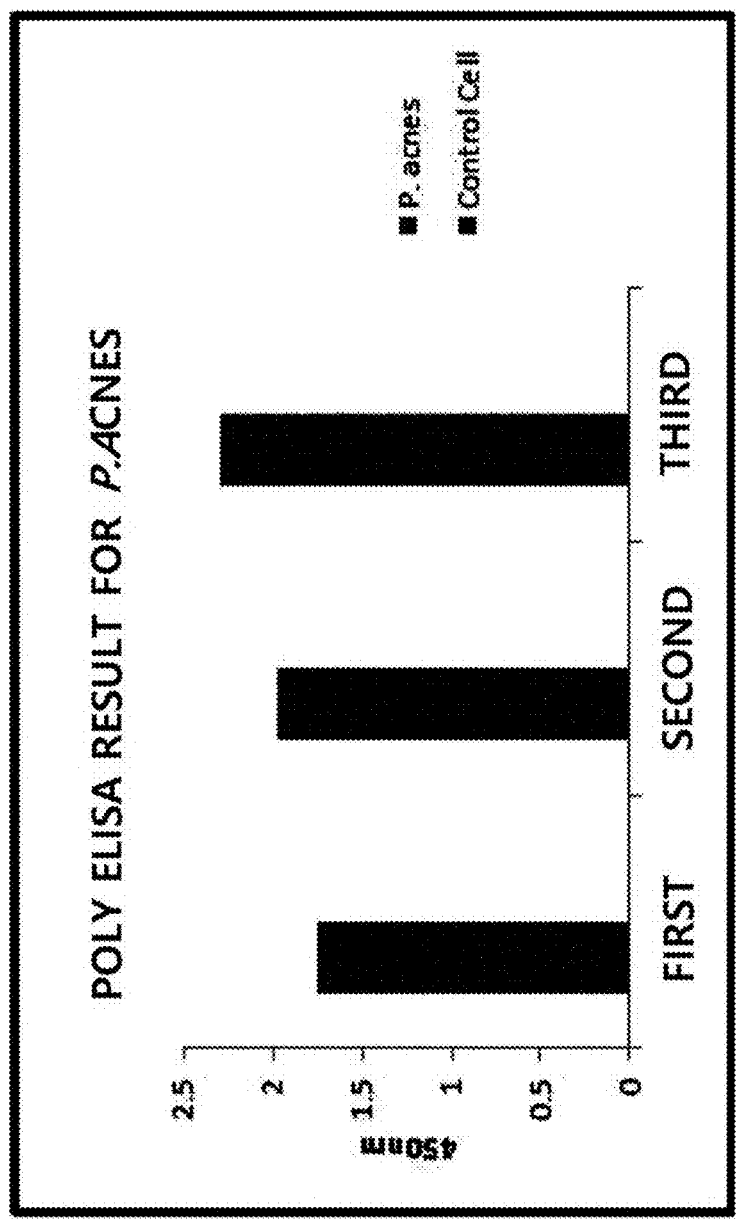
FIG. 4 is a graph showing a poly-scFv-phage ELISA result according to an exemplary embodiment.

As a result, Table 2 below and FIG. 4 show that, as the number of times of performing panning increased, the binding affinity between the poly-scFv-phage and *P. acnes* increased, but the poly-scFv-phage did not bind to the control cells.

TABLE 2

| | Poly-scFv-phage | | |
| --- | --- | --- | --- |
| Component | First | Second | Third |
| Acne-inducing bacteria | 1.7577 | 1.9688 | 2.3001 |
| Control cells | 0.0007 | 0.0030 | 0.0006 |

Figure 5:
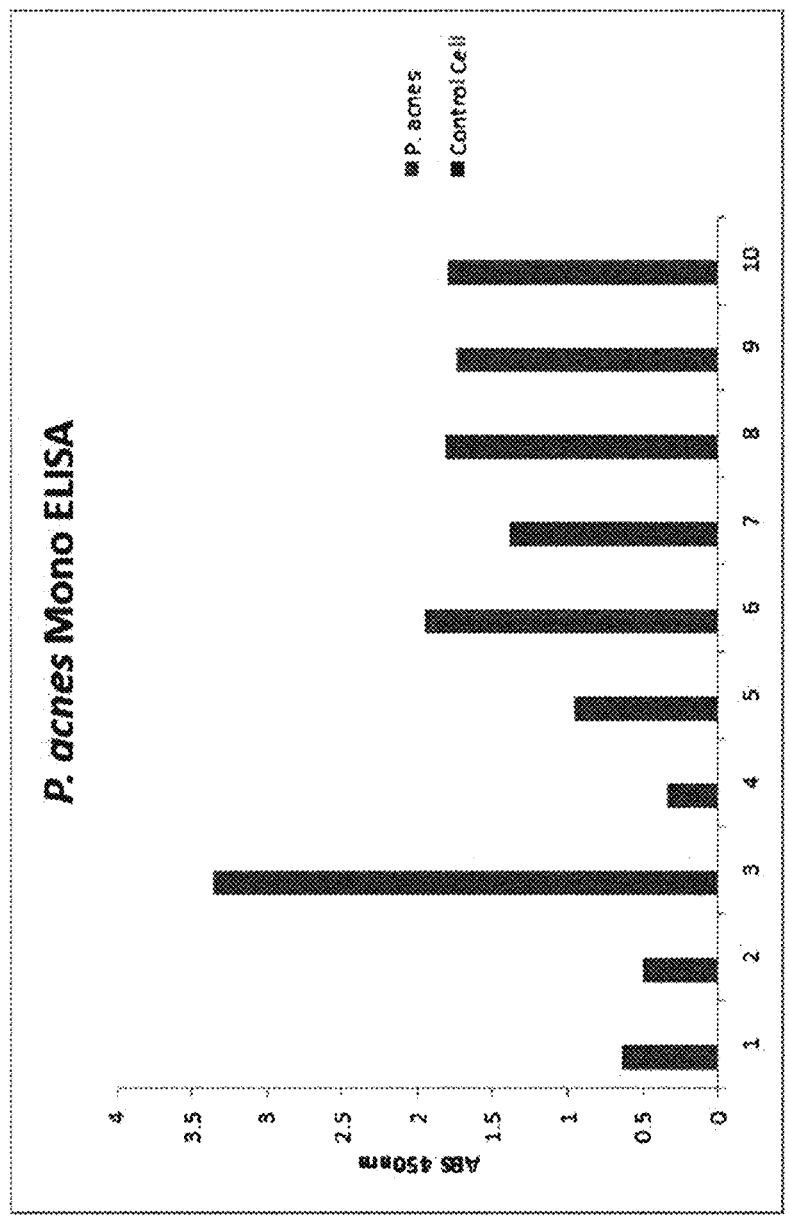
FIG. 5 is a graph showing a Mono-scFv-phage ELISA result according to an exemplary embodiment of the present invention.

<2-2> Selection of Mono Phage with High Binding Affinity from *P. acnes*-Binding Antibody Candidate Group From the *P. acnes*-binding poly-scFv-phage obtained in Step <2-1>, 10 mono phages with high affinity were selected. The selected mono phages were subjected to ELISA, again, to determine the binding affinity for *P. acnes* (FIG. 5).

TABLE 3

| No. | Acne-inducing bacteria (O.D. 450 nm) | Control cells (O.D. 450 nm) |
| --- | --- | --- |
| 1 | 0.6452 | 0.0005 |
| 2 | 0.504 | 0.0005 |
| 3 | 3.3563 | 0.0002 |
| 4 | 0.3394 | 0.0005 |
| 5 | 0.9509 | 0 |
| 6 | 1.9520 | 0.0041 |
| 7 | 1.3853 | 0.0013 |
| 8 | 1.8153 | 0.0044 |
| 9 | 1.7336 | 0.0012 |
| 10 | 1.8062 | 0.0023 |

<2-3> Sequencing for Selected Mono Phages

The obtained 10 mono-scFv-phages were classified according to sequence homology through sequencing. As a result, Table 4 below shows that clones No. 3, 6, 7, 8, 9 and 10 have different CDR3s without redundancy. As a result of determining the binding affinity for *P. acnes* through ELISA, it was confirmed that a total of four clones, No. 3, 6, 8 and 10, have the highest binding affinity.

TABLE 4

| No. | VH | Homology level | VL | Homology level | VH (CDR3-a.a seq) | VL (CDR3-a.a seq) | ELISA O.D. value |
|---|---|---|---|---|---|---|---|
| 3 | VH1-2 | 272/295 (92.2%) | V3-4 | 281/293 (95.9%) | VKGLEHAAGSAIFDR | ALSMGSGIWV | 3.6234 |
| 6 | VH3-20 | 273/387 (95.1%) | A23 | 291/299 (97.3%) | STRHLHH | VQAKQFPLT | 2.2191 |
| 7 | VH1-69 | 267/304 (87.8%) | L5 | 257/286 (89.9%) | ARAVDTAMVGDS | QQVDSYPLT | 1.6524 |
| 8 | VH3-9 | 267/294 (90.8%) | L5 | 268/294 (94.7%) | TTDLGVVPAAIYAFDI | QQTATFQIT | 2.0824 |
| 9 | VH3-74 | 276/295 (93.6%) | A23 | 281/299 (94.0%) | ARDDGATWLHDY | ARDDGATWLHDY | 2.0007 |
| 10 | VH3-53 | 262/284 (92.3%) | V2-14 | 252/289 (87.2%) | SCEGKAVSGSRDLHFEF | QVWDSSSDHLI | 2.0733 |

Example 3

Figure 6:
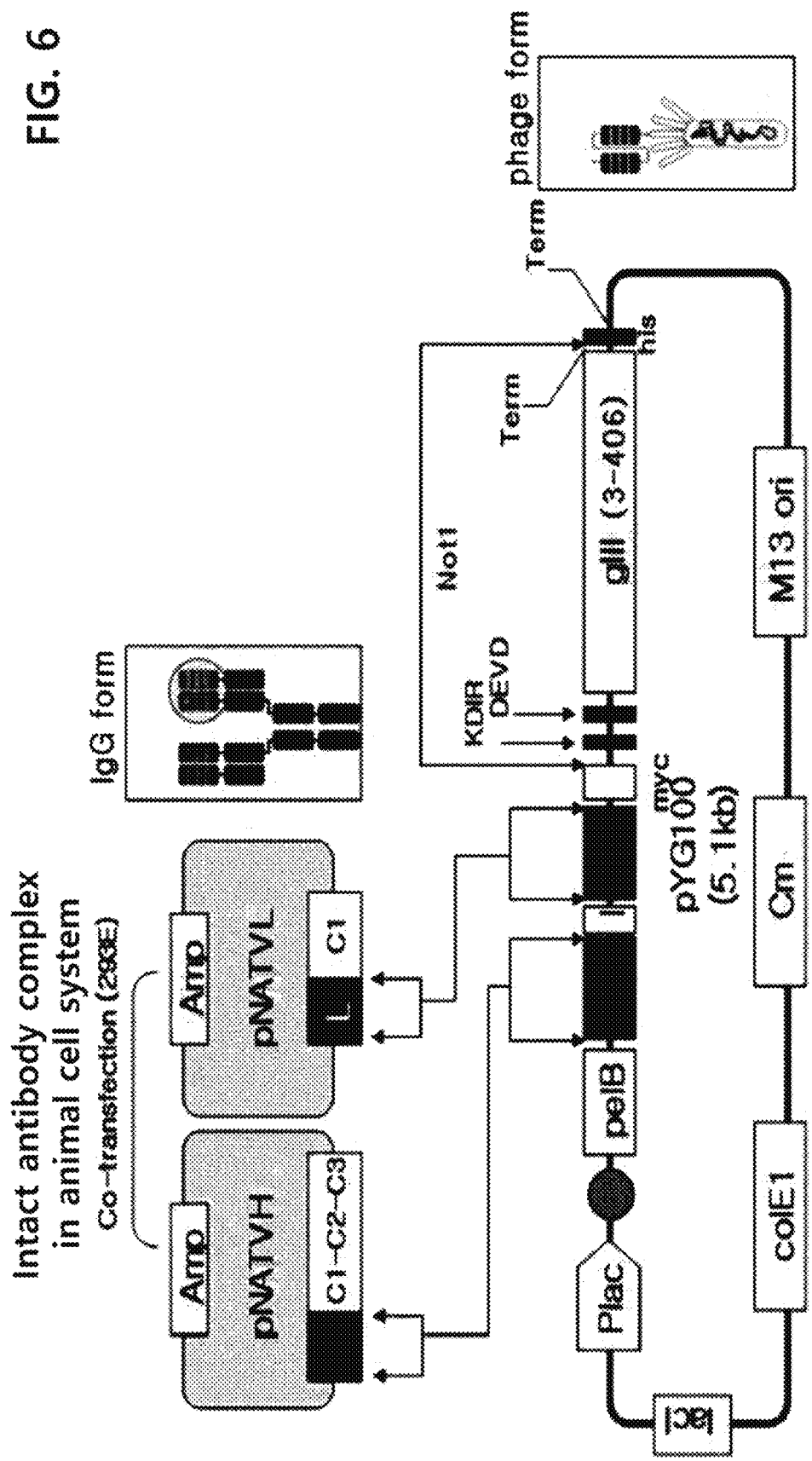
FIG. 6 is a diagram illustrating a method of conversion into an IgG form according to an exemplary embodiment of the present invention.
Figure 7B:
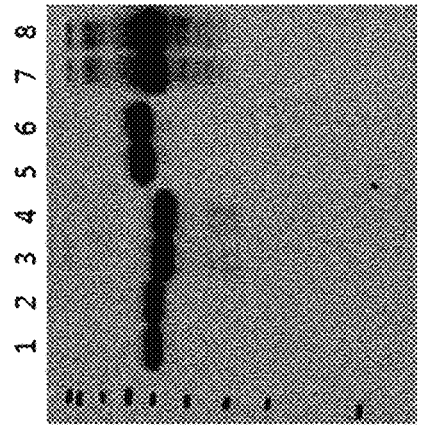
FIGS. 7A-7B show experimental data for the expression and purification of human antibodies according to an exemplary embodiment of the present invention.
Figure 7A:
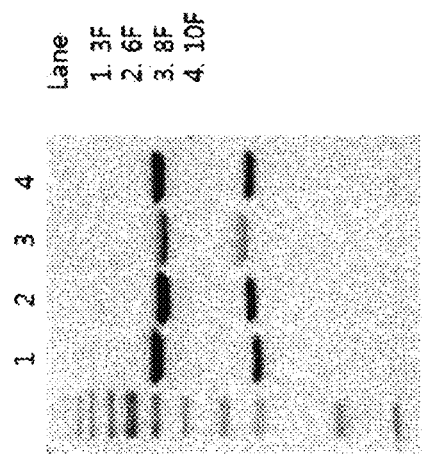

Expression and Purification of *P. acnes*-Specific Human Monoclonal Antibody To convert the obtained four clones with high affinity for *P. acnes* from an scFv type to an IgG type of a human antibody, a heavy chain and a light chain were cloned into each of animal cell expression vectors pNATVH and pNATVL (FIG. 6). The cloned expression vector was introduced into *E. coli*, thereby amplifying the vector. Each of the amplified 8 types of plasmids was co-transfected into HEK293F cells, cultured for 6 days, and subjected to Protein A affinity chromatography, thereby purifying and recovering an expressed antibody. The purified antibody protein was subjected to SDS-PAGE to determine a molecular weight and a pure culture isolation level (FIG. 7A). Afterward, western blotting was performed using an anti-Fc-HRP antibody as a secondary antibody, thereby confirming the production of a humanized monoclonal antibody (FIG. 7B).

The CDR region sequences and variable region sequences of the light chain and heavy chain of the produced monoclonal antibodies are shown in Table 5 below.

TABLE 5

| Antibody name | SEQ ID NO: | Sequence Name | Amino acid sequence |
|---|---|---|---|
| 3F | 1 | CDRH1 | GYTFTDYY |
|  | 2 | CDRH2 | INPNSGAP |
|  | 3 | CDRH3 | VKGLEHAAGSAIFDR |
|  | 4 | CDRL1 | SGSVSTSHF |
|  | 5 | CDRL2 | FKD |
|  | 6 | CDRL3 | ALSMGSGIWV |
| 6F | 7 | CDRH1 | GFTFDDHG |
|  | 8 | CDRH2 | INLNGGST |
|  | 9 | CDRH3 | STRHLHH |
|  | 10 | CDRL1 | QSLVHSNGNTY |
|  | 11 | CDRL2 | KIS |
|  | 12 | CDRL3 | VQAKQFPLT |
| 8F | 13 | CDRH1 | GFSFNDYA |
|  | 14 | CDRH2 | ISWNSRST |
|  | 15 | CDRH3 | TTDLGVVPAAIYAFDI |
|  | 16 | CDRL1 | QGITNW |
|  | 17 | CDRL2 | AAS |
|  | 18 | CDRL3 | QQTATFQIT |
| 10F | 19 | CDRH1 | GFTVSSSF |
|  | 20 | CDRH2 | AYSGGNT |
|  | 21 | CDRH3 | SCEGKAVSGSRDLHFEF |
|  | 22 | CDRL1 | NLRTKY |
|  | 23 | CDRL2 | NDN |
|  | 24 | CDRL3 | QVWDSSSDHLI |
| 3F | 25 | VH heavy chain variable region | QMQLVQSGAEVKKPGASVKVSCKASGYTFTDYYI HWVRQAPGQGLEWMGWINPNSGAPEFAQRFQGR VSMTRDASINTTYMELSGLRSEDTAVYYCVKGLE HAAGSAIFDRWGQGTMVTVSS |

TABLE 5-continued

| Antibody name | SEQ ID NO: | Sequence Name | Amino acid sequence |
|---|---|---|---|
| | 26 | VL light chain variable region | QTVVTQEPSFSVSPGGTVTLTCGLTSGSVSTSHFPS WYQQTPGQAPRTLIYFKDTRSSGVPDRFSGSILGN KAALTITGAQADDESDYYCALSMGSGIWVFGGGT KLTVL |
| 6F | 27 | VH heavy chain variable region | QVQLVESGGGVVRPGGSLRLSCTASGFTFDDHGM SWVRQAPGKGLEWVSTINLNGGSTAYADSVKGRF TISRDNAKNSLYLQMNSLRAEDTAVYYCSTRHLH HWGQGTLVTVSS |
| | 28 | VL light chain variable region | DIVMTQTPLSSPVTLGQPASISCRSSQSLVHSNGNT YLTWLQQRPGQPPRLLIHKISNRFSGVPDRFSGSG AGTDFTLKISRVEAEDVGVYYCVQAKQFPLTFGQ GTRLEIK |
| 8F | 29 | VH heavy chain variable region | QVQLVQSGGGVVQPGGSLRLSCAASGFSFNDYAM HWVRQVPGKGLEWVSSISWNSRSTVYAASVEGRF SISRDNSKNSLYLQMNSLRAEDAAVYYCTTDLGV VPAAIYAFDIWGQGTMVTVSS |
| | 30 | VL light chain variable region | DIQMTQSPSVMSASVGDRVNITCRASQGITNWLA WYQQKPGKAPKLLISAASSLQSGVPSRFSGSGSGT DFTLTISSLQPDDFATYYCQQTATFQITFGQGTRLDI K |
| 10F | 31 | VH heavy chain variable region | QVQLVESGGGLIQPGGSLRLSCVASGFTVSSSFMS WVRLAPGKGLEWVALAYSGGNTYYADSVKGRFT VSRDDSSNTLYLQMNSLRAEDTAVYYCSCEGKAV SGSRDLHFEFWSPGTLVTVSS |
| | 32 | VL light chain variable region | SYELTQAPSLSVSPGQTANIICSGDNLRTKYVSWY QQKPGQAPVLVIYNDNDRPSGIPERFSGTNSGNTA ALTISRVEAGDEADYYCQVWDSSSDHLIFGGGTKL TVL |

Example 4

Confirmation of Affinity of Human Monoclonal Antibody for *P. acnes*

ELISA was performed to confirm the affinity of the monoclonal antibody produced in the present invention for *P. acnes*.

Figure 8:
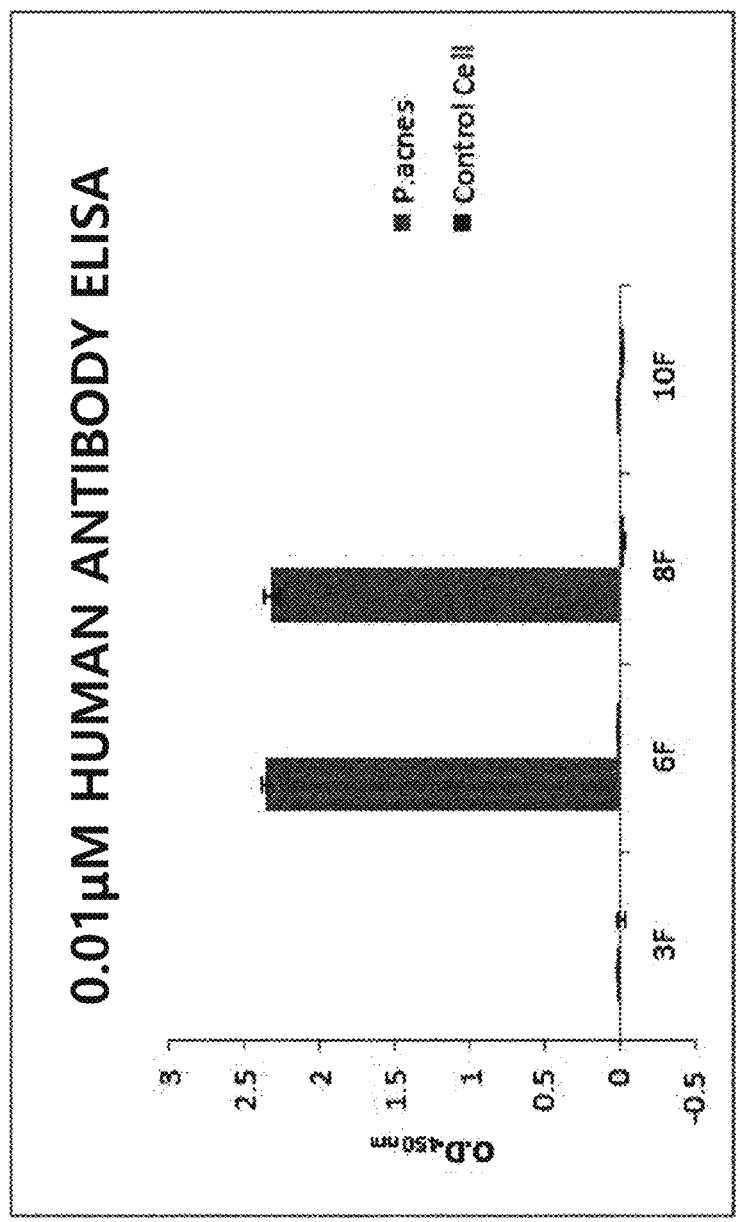
FIG. 8 is a graph showing an ELISA result concerning affinity between a human antibody produced according to an exemplary embodiment of the present invention and *P. acnes*.
Figure 9:
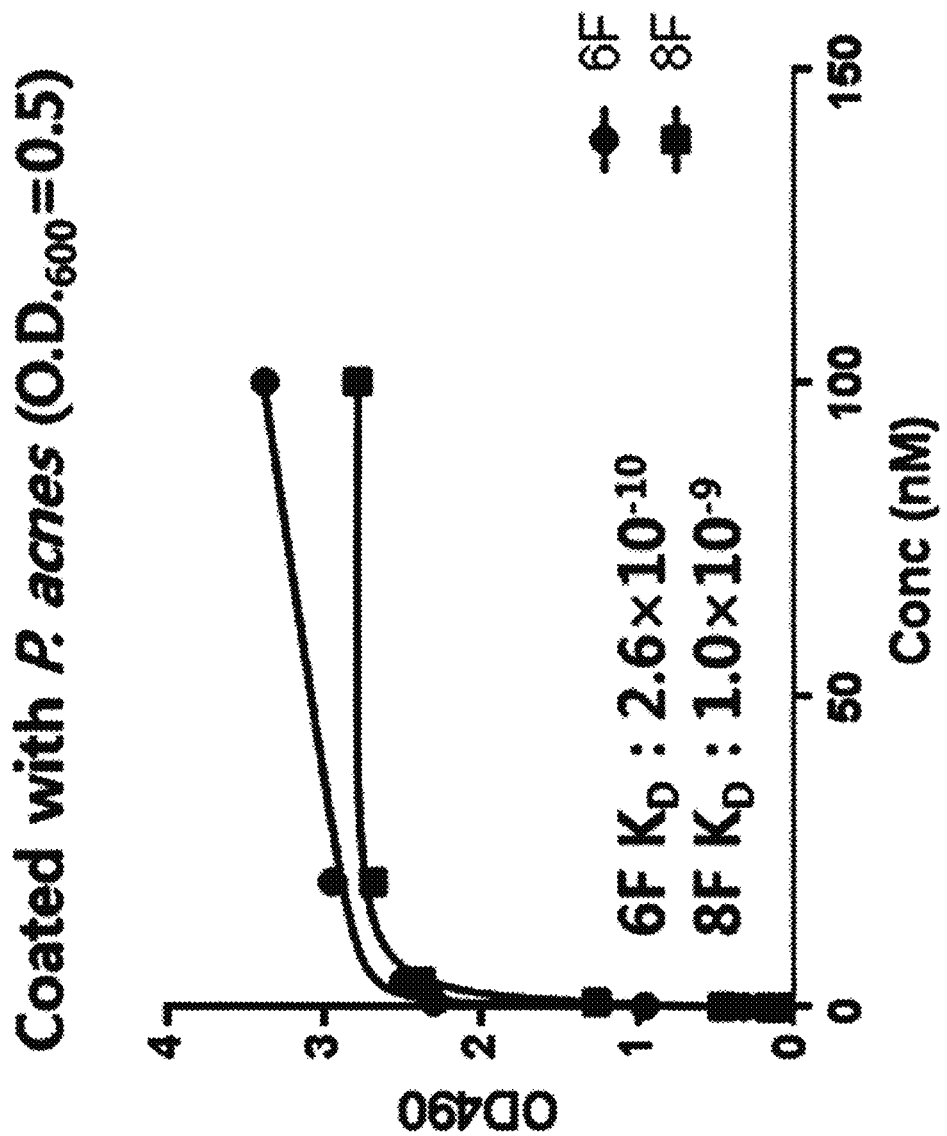
FIG. 9 is a graph showing an ELISA-derived result of analyzing affinity between a human antibody produced according to an exemplary embodiment of the present invention and *P. acnes*.

As a result, Table 6 below and FIGS. 8 and 9 show that a total of four types of antibodies (3F, 6F, 8F and 10F) have binding affinity for *P. acnes*, compared with all control cells, and particularly, the 6F antibody and 8F antibody have superior binding affinity for *P. acnes*. The dissolution constant ($K_D$) of each type of antibody was calculated using the value obtained by ELISA, and the $K_D$ of 6F was calculated as $2.6 \times 10^{-10}$ and the $K_D$ of 8F was calculated as $1.0 \times 10^{-9}$, which are far lower than $K_D = 10^{-6}$. This shows that 6F antibody and 8F antibody to *P. acnes* have high affinity (FIG. 9).

TABLE 6

| Antibody name | Acne-inducing bacteria (O.D. 450 nm) | Control cells (O.D. 450 nm) |
|---|---|---|
| 3F | 0.01495 | −0.01050 |
| 6F | 2.36215 | 0.01140 |
| 8F | 2.32065 | −0.02680 |
| 10F | 0.00605 | −0.02475 |

Example 5

Confirmation of Inhibitory Effect of Human Monoclonal Antibody on *P. acnes* Growth It was confirmed that the human antibody produced in the present invention has a significant effect of killing acne-inducing bacteria.

First, after *P. acnes* was seeded in a liquid medium and cultured overnight, the produced 6F antibody or 8F antibody was added at a concentration of 30 µg/mL, or a mixture of the same proportions of the 6F antibody and the 8F antibody was added at a concentration of 30 µg/mL, and then further incubated for 24 hours. Subsequently, the reacted medium was streaked on a solid medium and cultured overnight, and then the number of colonies formed was calculated. As a control, an untreated control treated with only PBS rather than an antibody and cultured for 24 hours under the same conditions was prepared. After the calculation of the colony number, a relative number of colonies in a 24-hour treated group, relative to the number of colonies before antibody treatment (0 hour), was calculated to calculate the growth rate of *P. acnes*.

Figure 10:
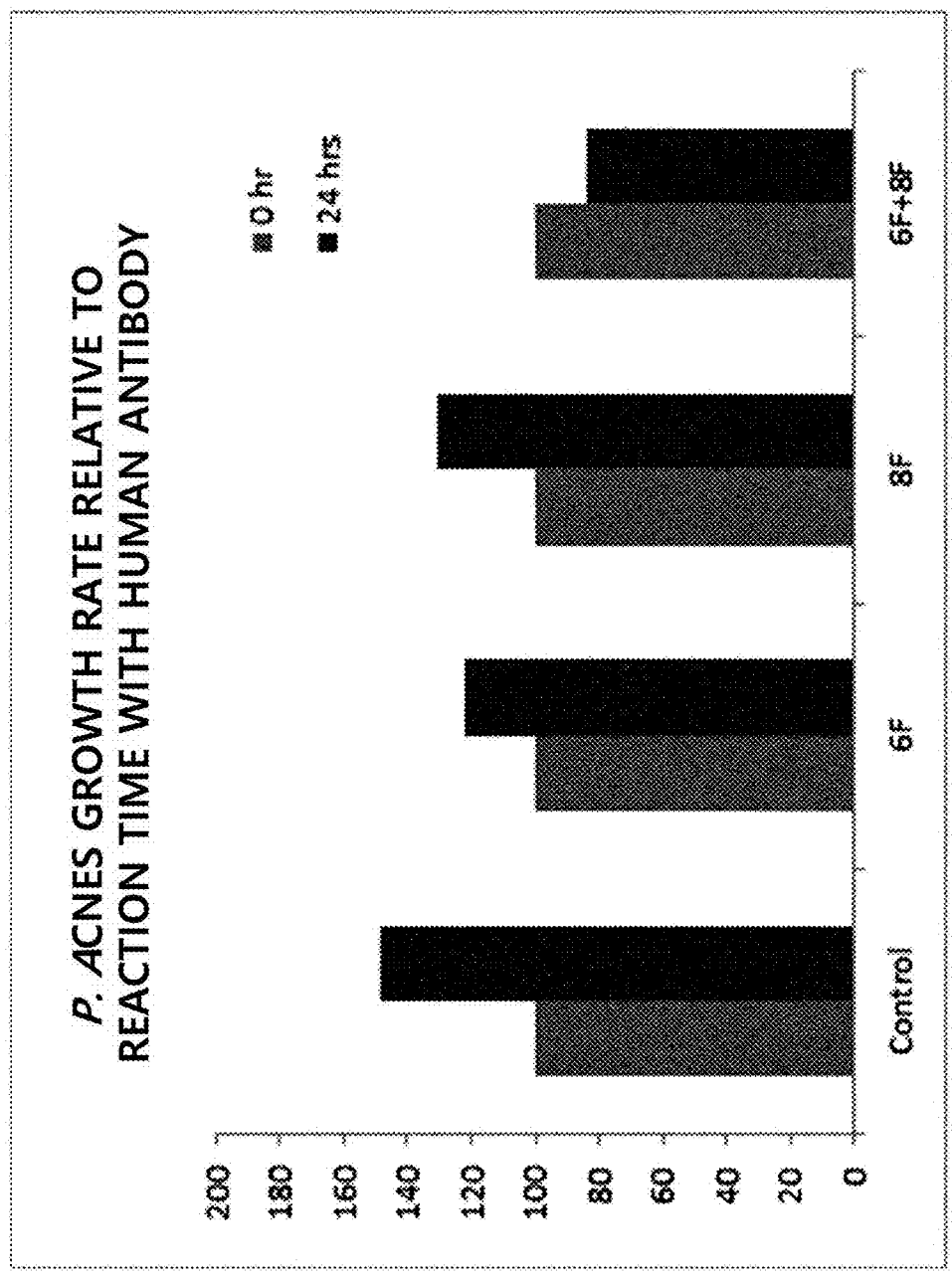
FIG. 10 is a graph showing a result of confirming an effect of a human antibody produced according to an exemplary embodiment of the present invention on inhibiting *P. acnes* growth.

As a result, referring to Table 7 below and FIG. 10, in the untreated control, the growth rate of *P. acnes* is approximately 150%, and in an experimental group to which the 6F antibody or 8F antibody is independently added, the growth rate of *P. acnes* is 122.2% or 130.8%, showing a significant decrease in growth rate, compared with the untreated control. In addition, in the experimental group treated with both the 6F antibody and 8F antibody, the growth rate of *P. acnes* is 83.5%, which is a decrease of 16.5% from the growth rate at 0 hour. It was confirmed that the synergistic effect of the inhibition of *P. acnes* growth is exhibited due to the cotreatment with the 6F and 8F antibodies, and a significant effect of killing acne-inducing bacteria can be exhibited.

TABLE 7

| Division | Growth rate relative to reaction time | | |
|---|---|---|---|
| | 0 hr | 24 hrs | Increment |
| Untreated control | 100% | 148.5% | +48.5% |
| 6F | 100% | 122.2% | +22.2% |
| 8F | 100% | 130.8% | +30.8% |
| 6F + 8F | 100% | 83.5% | −16.5% |

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

Preparation Examples for the compositions of the present invention will be described.

Preparation Example 1

Production of Cosmetics

<1-1> Skin Softener (Skin)

To produce a skin softener including the monoclonal antibody of the present invention, the following components as listed in Table 7 below may be mixed by a conventional production method used in the cosmetic field.

TABLE 8

| Component | Content (wt %) |
|---|---|
| Monoclonal antibody of the present invention | 0.1~30% |
| 1,3-butylene glycol | 3.0 |
| Glycerin | 5.0 |
| Polyoxyethylene (60) hydrogenated castor oil | 0.2 |
| Ethanol | 8.0 |
| Citric acid | 0.02 |
| Sodium citrate | 0.06 |
| Preservative | Trace |
| Fragrance | Trace |
| Distilled water | To 100 |

<1-2> Nourishing Toner (Lotion)

To produce a nourishing toner including the monoclonal antibody of the present invention, the following components as listed in Table 9 below may be mixed by a conventional production method used in the cosmetic field.

TABLE 9

| Component | Content (wt %) |
|---|---|
| Monoclonal antibody of the present invention | 0.1~30% |
| 1,3-butylene glycol | 8.0 |
| Glycerin | 5.0 |
| Squalane | 10.0 |
| Polyoxyethylene sorbitan monooleate | 2.0 |
| Guaiac oil | 0.1~30% |
| 1,3-butylene glycol | 3.0 |
| Glycerin | 5.0 |
| Polyoxyethylene (60) hydrogenated castor oil | 0.2 |
| Ethanol | 8.0 |
| Citric acid | 0.02 |
| Sodium citrate | 0.06 |

TABLE 9-continued

| Component | Content (wt %) |
|---|---|
| Preservative | Trace |
| Fragrance | Trace |
| Distilled water | To 100 |

<1-3> Essence

To produce an essence including the monoclonal antibody of the present invention, the following components as listed in Table 10 below may be mixed by a conventional production method used in the cosmetic field.

TABLE 10

| Component | Content (wt %) |
|---|---|
| Monoclonal antibody of the present invention | 0.1~30% |
| Sitosterol | 1.7 |
| Polyglyceryl-2-oleate | 1.5 |
| Ceramide | 0.7 |
| Steareth-4 | 1.2 |
| Cholesterol | 1.5 |
| Dicetyl phosphate | 0.4 |
| Concentrated glycerin | 5.0 |
| Carboxy vinyl polymer | 0.2 |
| Xanthan gum | 0.2 |
| Preservative | Trace |
| Fragrance | Trace |
| Distilled water | To 100 |

<1-4> Cleanser (Cleansing Foam)

To produce a cleanser (cleansing foam) including the monoclonal antibody of the present invention, the following components as listed in Table 11 below may be mixed by a conventional production method used in the cosmetic field.

TABLE 11

| Component | Content (wt %) |
|---|---|
| Human antibody of the present invention | 0.1~30% |
| N-sodium acylglutamate | 20.0 |
| Glycerin | 10.0 |
| PEG-400 | 15.0 |
| Propylene glycol | 10.0 |
| POE(15) oleyl alcohol ether | 3.0 |
| Laurin derivative | 2.0 |
| Methyl paraben | 0.2 |
| EDTA-4Na | 0.03 |
| Fragrance | 0.2 |
| Distilled water | To 100 |

<1-5> Nourishing Cream

To produce a nourishing cream including the monoclonal antibody of the present invention, the following components as listed in Table 12 below may be mixed by a conventional production method used in the cosmetic field.

TABLE 12

| Component | Content (wt %) |
|---|---|
| Peptide of the present invention | 0.1~30% |
| Vaseline | 7.0 |
| Liquid paraffin | 10.0 |
| Beeswax | 2.0 |
| Polysorbate 60 | 2.5 |
| Sorbitan sesquioleate | 1.5 |
| Squalane | 3.0 |
| Propylene glycol | 6.0 |
| Glycerin | 4.0 |
| Triethanolamine | 0.5 |

TABLE 12-continued

| Component | Content (wt %) |
| --- | --- |
| Xanthan gum | 0.5 |
| Tocopheryl acetate | 0.1 |
| Fragrance, Preservative | Trace |
| Distilled water | To 100 |

<1-6> Massage Cream

To produce a massage cream including the monoclonal antibody of the present invention, the following components as listed in Table 13 below may be mixed by a conventional production method used in the cosmetic field.

TABLE 13

| Component | Content (wt %) |
| --- | --- |
| Monoclonal antibody of the present invention | 0.1~30% |
| Propylene glycol | 6.0 |
| Glycerin | 4.0 |
| Triethanolamine | 0.5 |
| Beeswax | 2.0 |
| Tocopheryl acetate | 0.1 |
| Polysorbate 60 | 3.0 |
| Sorbitan sesquioleate | 2.5 |
| Cetearyl alcohol | 2.0 |
| Liquid paraffin | 30.0 |
| Xanthan gum | 0.5 |
| Fragrance, Preservative | Trace |
| Distilled water | To 100 |

<1-7> Pack

To produce a pack including the monoclonal antibody of the present invention, the following components as listed in Table 14 below may be mixed by a conventional production method used in the cosmetic field.

TABLE 14

| Component | Content (wt %) |
| --- | --- |
| Monoclonal antibody of the present invention | 0.1~30% |
| Propylene glycol | 2.0 |
| Glycerin | 4.0 |
| Poly vinyl alcohol | 10.0 |
| Ethanol | 7.0 |
| PEG-40 hydrogenated castor oil | 0.8 |
| Triethanolamine | 0.3 |
| Fragrance, Preservative | Trace |
| Distilled water | To 100 |

The present invention is not limited to the examples and preparation examples described above, may be modified and altered by those of ordinary skill in the art, may be applied to cosmetics for various uses including color cosmetics, and may be used to produce a drug thinly applied to the human body, that is, an ointment, according to its efficacy, and all modifications and alternations are included in the spirit and scope of the present invention as defined in the accompanying claims.

---

The invention claimed is:

1. A monoclonal antibody comprising a heavy chain variable region comprising the sequence set forth in SEQ ID NO: 27 and a light chain variable region comprising the sequence set forth in SEQ ID NO: 28, wherein the monoclonal antibody binds to *Propionibacterium acnes* (*P acnes*).

2. The monoclonal antibody of claim 1, wherein the monoclonal antibody is a human antibody.

3. A cosmetic composition comprising:
   the monoclonal antibody according to claim 1 as an active ingredient.

4. A pharmaceutical composition comprising:
   the monoclonal antibody according to claim 1 as an active ingredient and a pharmaceutically acceptable carrier.

5. A method of treating acne, comprising:
   administering a pharmaceutically acceptable amount of the monoclonal antibody according to claim 1 to a subject in need thereof.

* * * * *

SEQUENCE LISTING

```
<160> NUMBER OF SEQ ID NOS: 32

<210> SEQ ID NO 1
<211> LENGTH: 8
<212> TYPE: PRT
<213> ORGANISM: Artificial
<220> FEATURE:
<223> OTHER INFORMATION: CDRH1 OF 3F ANTIBODY

<400> SEQUENCE: 1

Gly Tyr Thr Phe Thr Asp Tyr Tyr
1               5

<210> SEQ ID NO 2
<211> LENGTH: 8
<212> TYPE: PRT
<213> ORGANISM: Artificial
<220> FEATURE:
<223> OTHER INFORMATION: CDRH2 OF 3F ANTIBODY

<400> SEQUENCE: 2

Ile Asn Pro Asn Ser Gly Ala Pro
1               5

<210> SEQ ID NO 3
<211> LENGTH: 15
<212> TYPE: PRT
<213> ORGANISM: Artificial
<220> FEATURE:
<223> OTHER INFORMATION: CDRH3 OF 3F ANTIBODY

<400> SEQUENCE: 3

Val Lys Gly Leu Glu His Ala Ala Gly Ser Ala Ile Phe Asp Arg
1               5                   10                  15
```

```
<210> SEQ ID NO 4
<211> LENGTH: 9
<212> TYPE: PRT
<213> ORGANISM: Artificial
<220> FEATURE:
<223> OTHER INFORMATION: CDRL1 OF 3F ANTIBODY

<400> SEQUENCE: 4

Ser Gly Ser Val Ser Thr Ser His Phe
1               5

<210> SEQ ID NO 5
<211> LENGTH: 3
<212> TYPE: PRT
<213> ORGANISM: Artificial
<220> FEATURE:
<223> OTHER INFORMATION: CDRL2 OF 3F ANTIBODY

<400> SEQUENCE: 5

Phe Lys Asp
1

<210> SEQ ID NO 6
<211> LENGTH: 10
<212> TYPE: PRT
<213> ORGANISM: Artificial
<220> FEATURE:
<223> OTHER INFORMATION: CDRL3 OF 3F ANTIBODY

<400> SEQUENCE: 6

Ala Leu Ser Met Gly Ser Gly Ile Trp Val
1               5                   10

<210> SEQ ID NO 7
<211> LENGTH: 8
<212> TYPE: PRT
<213> ORGANISM: Artificial
<220> FEATURE:
<223> OTHER INFORMATION: CDRH1 OF 6F ANTIBODY

<400> SEQUENCE: 7

Gly Phe Thr Phe Asp Asp His Gly
1               5

<210> SEQ ID NO 8
<211> LENGTH: 8
<212> TYPE: PRT
<213> ORGANISM: Artificial
<220> FEATURE:
<223> OTHER INFORMATION: CDRH2 OF 6F ANTIBODY

<400> SEQUENCE: 8

Ile Asn Leu Asn Gly Gly Ser Thr
1               5

<210> SEQ ID NO 9
<211> LENGTH: 7
<212> TYPE: PRT
<213> ORGANISM: Artificial
<220> FEATURE:
<223> OTHER INFORMATION: CDRH3 OF 6F ANTIBODY

<400> SEQUENCE: 9

Ser Thr Arg His Leu His His
1               5
```

```
<210> SEQ ID NO 10
<211> LENGTH: 11
<212> TYPE: PRT
<213> ORGANISM: Artificial
<220> FEATURE:
<223> OTHER INFORMATION: CDRL1 OF 6F ANTIBODY

<400> SEQUENCE: 10

Gln Ser Leu Val His Ser Asn Gly Asn Thr Tyr
1               5                   10

<210> SEQ ID NO 11
<211> LENGTH: 3
<212> TYPE: PRT
<213> ORGANISM: Artificial
<220> FEATURE:
<223> OTHER INFORMATION: CDRL2 OF 6F ANTIBODY

<400> SEQUENCE: 11

Lys Ile Ser
1

<210> SEQ ID NO 12
<211> LENGTH: 9
<212> TYPE: PRT
<213> ORGANISM: Artificial
<220> FEATURE:
<223> OTHER INFORMATION: CDRL3 OF 6F ANTIBODY

<400> SEQUENCE: 12

Val Gln Ala Lys Gln Phe Pro Leu Thr
1               5

<210> SEQ ID NO 13
<211> LENGTH: 8
<212> TYPE: PRT
<213> ORGANISM: Artificial
<220> FEATURE:
<223> OTHER INFORMATION: CDRH1 OF 8F ANTIBODY

<400> SEQUENCE: 13

Gly Phe Ser Phe Asn Asp Tyr Ala
1               5

<210> SEQ ID NO 14
<211> LENGTH: 8
<212> TYPE: PRT
<213> ORGANISM: Artificial
<220> FEATURE:
<223> OTHER INFORMATION: CDRH2 OF 8F ANTIBODY

<400> SEQUENCE: 14

Ile Ser Trp Asn Ser Arg Ser Thr
1               5

<210> SEQ ID NO 15
<211> LENGTH: 16
<212> TYPE: PRT
<213> ORGANISM: Artificial
<220> FEATURE:
<223> OTHER INFORMATION: CDRH3 OF 8F ANTIBODY

<400> SEQUENCE: 15

Thr Thr Asp Leu Gly Val Val Pro Ala Ala Ile Tyr Ala Phe Asp Ile
1               5                   10                  15

<210> SEQ ID NO 16
```

```
<211> LENGTH: 6
<212> TYPE: PRT
<213> ORGANISM: Artificial
<220> FEATURE:
<223> OTHER INFORMATION: CDRL1 OF 8F ANTIBODY

<400> SEQUENCE: 16

Gln Gly Ile Thr Asn Trp
1               5

<210> SEQ ID NO 17
<211> LENGTH: 3
<212> TYPE: PRT
<213> ORGANISM: Artificial
<220> FEATURE:
<223> OTHER INFORMATION: CDRL2 OF 8F ANTIBODY

<400> SEQUENCE: 17

Ala Ala Ser
1

<210> SEQ ID NO 18
<211> LENGTH: 9
<212> TYPE: PRT
<213> ORGANISM: Artificial
<220> FEATURE:
<223> OTHER INFORMATION: CDRL3 OF 8F ANTIBODY

<400> SEQUENCE: 18

Gln Gln Thr Ala Thr Phe Gln Ile Thr
1               5

<210> SEQ ID NO 19
<211> LENGTH: 8
<212> TYPE: PRT
<213> ORGANISM: Artificial
<220> FEATURE:
<223> OTHER INFORMATION: CDRH1 OF 10F ANTIBODY

<400> SEQUENCE: 19

Gly Phe Thr Val Ser Ser Ser Phe
1               5

<210> SEQ ID NO 20
<211> LENGTH: 7
<212> TYPE: PRT
<213> ORGANISM: Artificial
<220> FEATURE:
<223> OTHER INFORMATION: CDRH2 OF 10F ANTIBODY

<400> SEQUENCE: 20

Ala Tyr Ser Gly Gly Asn Thr
1               5

<210> SEQ ID NO 21
<211> LENGTH: 17
<212> TYPE: PRT
<213> ORGANISM: Artificial
<220> FEATURE:
<223> OTHER INFORMATION: CDRH3 OF 10F ANTIBODY

<400> SEQUENCE: 21

Ser Cys Glu Gly Lys Ala Val Ser Gly Ser Arg Asp Leu His Phe Glu
1               5                   10                  15
Phe
```

```
<210> SEQ ID NO 22
<211> LENGTH: 6
<212> TYPE: PRT
<213> ORGANISM: Artificial
<220> FEATURE:
<223> OTHER INFORMATION: CDRL1 OF 10F ANTIBODY

<400> SEQUENCE: 22

Asn Leu Arg Thr Lys Tyr
1               5

<210> SEQ ID NO 23
<211> LENGTH: 3
<212> TYPE: PRT
<213> ORGANISM: Artificial
<220> FEATURE:
<223> OTHER INFORMATION: CDRL2 OF 10F ANTIBODY

<400> SEQUENCE: 23

Asn Asp Asn
1

<210> SEQ ID NO 24
<211> LENGTH: 11
<212> TYPE: PRT
<213> ORGANISM: Artificial
<220> FEATURE:
<223> OTHER INFORMATION: CDRL3 OF 10F ANTIBODY

<400> SEQUENCE: 24

Gln Val Trp Asp Ser Ser Ser Asp His Leu Ile
1               5                   10

<210> SEQ ID NO 25
<211> LENGTH: 122
<212> TYPE: PRT
<213> ORGANISM: Artificial
<220> FEATURE:
<223> OTHER INFORMATION: 3F HEAVY CHAIN VARIABLE REGION(VH)

<400> SEQUENCE: 25

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Gly Trp Ile Asn Pro Asn Ser Gly Ala Pro Gly Phe Ala Gln Arg Phe
        50                  55                  60

Gln Gly Arg Val Ser Met Thr Arg Asp Ala Ser Ile Asn Thr Thr Tyr
65                  70                  75                  80

Met Glu Leu Ser Gly Leu Arg Ser Glu Asp Thr Ala Val Tyr Tyr Cys
                85                  90                  95

Val Lys Gly Leu Glu His Ala Ala Gly Ser Ala Ile Phe Asp Arg Trp
            100                 105                 110

Gly Gln Gly Thr Met Val Thr Val Ser Ser
        115                 120

<210> SEQ ID NO 26
<211> LENGTH: 110
<212> TYPE: PRT
<213> ORGANISM: Artificial
<220> FEATURE:
<223> OTHER INFORMATION: 3F LIGHT CHAIN VARIABLE REGION(VL)
```

<400> SEQUENCE: 26

Gln Thr Val Val Thr Gln Glu Pro Ser Phe Ser Val Ser Pro Gly Gly
1               5                   10                  15

Thr Val Thr Leu Thr Cys Gly Leu Thr Ser Gly Ser Val Ser Thr Ser
            20                  25                  30

His Phe Pro Ser Trp Tyr Gln Gln Thr Pro Gly Gln Ala Pro Arg Thr
        35                  40                  45

Leu Ile Tyr Phe Lys Asp Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Ser Met Gly Ser
                85                  90                  95

Gly Ile Trp Val Phe Gly Gly Gly Thr Lys Leu Thr Val Leu
            100                 105                 110

<210> SEQ ID NO 27
<211> LENGTH: 114
<212> TYPE: PRT
<213> ORGANISM: Artificial
<220> FEATURE:
<223> OTHER INFORMATION: 6F HEAVY CHAIN VARIABLE REGION(VH)

<400> SEQUENCE: 27

Gln Val Gln Leu Val Glu Ser Gly Gly Gly Val Val Arg Pro Gly Gly
1               5                   10                  15

Ser Leu Arg Leu Ser Cys Thr Ala Ser Gly Phe Thr Phe Asp Asp His
            20                  25                  30

Gly Met Ser Trp Val Arg Gln Ala Pro Gly Lys Gly Leu Glu Trp Val
        35                  40                  45

Ser Thr Ile Asn Leu Asn Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ser Thr Arg His Leu His His Trp Gly Gln Gly Thr Leu Val Thr Val
            100                 105                 110

Ser Ser

<210> SEQ ID NO 28
<211> LENGTH: 112
<212> TYPE: PRT
<213> ORGANISM: Artificial
<220> FEATURE:
<223> OTHER INFORMATION: 6F LIGHT CHAIN VARIABLE REGION(VL)

<400> SEQUENCE: 28

Asp Ile Val Met Thr Gln Thr Pro Leu Ser Ser Pro Val Thr Leu Gly
1               5                   10                  15

```
Gln Pro Ala Ser Ile Ser Cys Arg Ser Ser Gln Ser Leu Val His Ser
            20                  25                  30

Asn Gly Asn Thr Tyr Leu Thr Trp Leu Gln Gln Arg Pro Gly Gln Pro
        35                  40                  45

Pro Arg Leu Leu Ile His Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Lys Gln Phe Pro Leu Thr Phe Gly Gln Gly Thr Arg Leu Glu Ile Lys
            100                 105                 110

<210> SEQ ID NO 29
<211> LENGTH: 123
<212> TYPE: PRT
<213> ORGANISM: Artificial
<220> FEATURE:
<223> OTHER INFORMATION: 8F HEAVY CHAIN VARIABLE REGION(VH)

<400> SEQUENCE: 29

Gln Val Gln Leu Val Gln Ser Gly Gly Gly Val Val Gln Pro Gly Gly
1               5                   10                  15

Ser Leu Arg Leu Ser Cys Ala Ala Ser Gly Phe Ser Phe Asn Asp Tyr
            20                  25                  30

Ala Met His Trp Val Arg Gln Val Pro Gly Lys Gly Leu Glu Trp Val
        35                  40                  45

Ser Ser Ile Ser Trp Asn Ser Arg Ser Thr Val Tyr Ala Ala Ser Val
    50                  55                  60

Glu Gly Arg Phe Ser Ile Ser Arg Asp Asn Ser Lys Asn Ser Leu Tyr
65                  70                  75                  80

Leu Gln Met Asn Ser Leu Arg Ala Glu Asp Ala Ala Val Tyr Tyr Cys
                85                  90                  95

Thr Thr Asp Leu Gly Val Val Pro Ala Ala Ile Tyr Ala Phe Asp Ile
            100                 105                 110

Trp Gly Gln Gly Thr Met Val Thr Val Ser Ser
            115                 120

<210> SEQ ID NO 30
<211> LENGTH: 107
<212> TYPE: PRT
<213> ORGANISM: Artificial
<220> FEATURE:
<223> OTHER INFORMATION: 8F LIGHT CHAIN VARIABLE REGION(VL)

<400> SEQUENCE: 30

Asp Ile Gln Met Thr Gln Ser Pro Ser Val Met Ser Ala Ser Val Gly
1               5                   10                  15

Asp Arg Val Asn Ile Thr Cys Arg Ala Ser Gln Gly Ile Thr Asn Trp
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Thr Ala Thr Phe Gln Ile
                85                  90                  95
```

Thr Phe Gly Gln Gly Thr Arg Leu Asp Ile Lys
            100                 105

<210> SEQ ID NO 31
<211> LENGTH: 123
<212> TYPE: PRT
<213> ORGANISM: Artificial
<220> FEATURE:
<223> OTHER INFORMATION: 10F HEAVY CHAIN VARIABLE REGION(VH)

<400> SEQUENCE: 31

Gln Val Gln Leu Val Glu Ser Gly Gly Gly Leu Ile Gln Pro Gly Gly
1               5                   10                  15

Ser Leu Arg Leu Ser Cys Val Ala Ser Gly Phe Thr Val Ser Ser Ser
            20                  25                  30

Phe Met Ser Trp Val Arg Leu Ala Pro Gly Lys Gly Leu Glu Trp Val
        35                  40                  45

Ala Leu Ala Tyr Ser Gly Gly Asn Thr Tyr Tyr Ala Asp Ser Val Lys
    50                  55                  60

Gly Arg Phe Thr Val Ser Arg Asp Asp Ser Ser Asn Thr Leu Tyr Leu
65                  70                  75                  80

Gln Met Asn Ser Leu Arg Ala Glu Asp Thr Ala Val Tyr Tyr Cys Ser
                85                  90                  95

Cys Glu Gly Lys Ala Val Ser Gly Ser Arg Asp Leu His Phe Glu Phe
            100                 105                 110

Trp Ser Pro Gly Thr Leu Val Thr Val Ser Ser
        115                 120

<210> SEQ ID NO 32
<211> LENGTH: 108
<212> TYPE: PRT
<213> ORGANISM: Artificial
<220> FEATURE:
<223> OTHER INFORMATION: 10F LIGHT CHAIN VARIABLE REGION(VL)

<400> SEQUENCE: 32

Ser Tyr Glu Leu Thr Gln Ala Pro Ser Leu Ser Val Ser Pro Gly Gln
1               5                   10                  15

Thr Ala Asn Ile Ile Cys Ser Gly Asp Asn Leu Arg Thr Lys Tyr Val
            20                  25                  30

Ser Trp Tyr Gln Gln Lys Pro Gly Gln Ala Pro Val Leu Val Ile Tyr
        35                  40                  45

Asn Asp Asn Asp Arg Pro Ser Gly Ile Pro Glu Arg Phe Ser Gly Thr
    50                  55                  60

Asn Ser Gly Asn Thr Ala Ala Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Leu Ile Phe Gly Gly Gly Thr Lys Leu Thr Val Leu
            100                 105